United States Patent [19]

Ellames et al.

[11] Patent Number: 4,696,928

[45] Date of Patent: Sep. 29, 1987

[54] SUBSTITUTED DIHYDROIMIDAZO[1,2-A]QUINOXALINES

[75] Inventors: George J. Ellames, High Wycombe; Albert A. Jaxa-Chamiec, Marlow, both of United Kingdom

[73] Assignee: G. D. Searle & Co., Chicago, Ill.

[21] Appl. No.: 774,218

[22] Filed: Sep. 9, 1985

[51] Int. Cl.$^4$ .................. C07D 487/04; C07D 487/14; A61K 31/495
[52] U.S. Cl. ..................................... 514/250; 544/346
[58] Field of Search ......................... 544/346; 514/250

[56] References Cited

U.S. PATENT DOCUMENTS 4,440,929  4/1984  Lee et al. ............................. 544/346
4,474,784  10/1984 Barnes ................................. 544/346

Primary Examiner—Mark L. Berch
Attorney, Agent, or Firm—Mary Jo Kanady; Paul D. Matukaitis

[57] ABSTRACT

This disclosure relates to a novel class of substituted dihydroimidazo[1,2-a]quinoxaline derivatives. The disclosure further relates to pharmaceutical compositions containing such compounds and to the use of such compounds and compositions as anti-anaerobic agents.

18 Claims, No Drawings

SUBSTITUTED DIHYDROIMIDAZO[1,2-A]QUINOXALINES

This invention relates to a novel class of substituted dihydroimidazo[1,2-a]quinoxaline derivatives. The present invention further relates to pharmaceutical compositions containing such compounds and to the use of such compounds and compositions as anti-anaerobic agents.

BACKGROUND OF THE INVENTION

Parthasarathy, et al., *Indian Journal of Chemistry* Vol. 22B (December 1983) p.1250–1251, describe a class of substituted 1,2-dihydroimidazo[1,2-a]quinoxaline 5-oxides that have antiamoebic activity against *Entamoeba histolytica* in intestinal and hepatic amoebiasis. Parthasarathy, et al., *Indian Journal of Chemistry* Vol. 22B (December 1983) p.1233–1235 describe certain N-oxides of 2,3-dihydro-1H-pyrimido[2,1-h]pteridines; 1,2-dihydroimidazo[2,1-h]pteridines; 10-aza-2,3-dihydro-1H-pyrimido[1,2-a]quinoxalines; 9-aza-1,2-dihydroimidazo[1,2-a]quinoxalines and 7-aza-1,2-dihydroimidazo[1,2-a]quinoxalines which possess antiamoebic activity in particular against hepatic amoebiasis. Strauss, et al., *J Org Chem*, Vol 43, No 10, 1978 p.2041–2044 describe the preparation of quinoxaline and dihydroimidazoquinoxaline N-oxides.

SUMMARY OF THE INVENTION

The present invention relates to a class of novel compounds of the formula

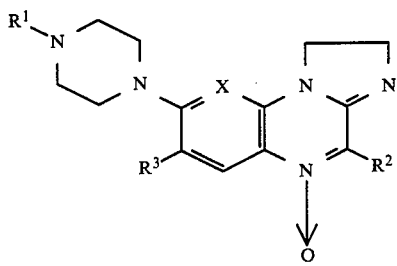

(I)

wherein
$R^1$ is $C_1$–$C_6$ alkyl, benzyl, phenyl,

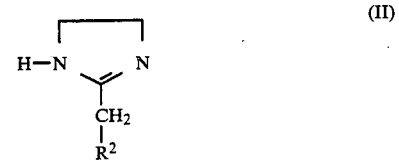

wherein $R^4$ is $C_1$–$C_6$ alkyl, and $R^5$ is $C_1$–$C_8$ alkyl, aminomethyl, pyridinyl, phenyl, halophenyl of a

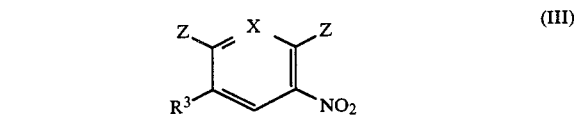

wherein $R^6$ is $C_1$–$C_6$ alkyl;
$R^2$ is phenyl or substituted phenyl having 1 or 2 substituents selected from the class consisting of halo or $C_1$–$C_6$ alkoxy.
$R^3$ is hydrogen or halogen; and X is —CH— or —N—.

The present invention further relates to pharmaceutical compositions containing such compounds and to the use of such compounds as anti-anaerobic agents.

DETAILED DESCRIPTION OF THE INVENTION

The "$C_1$–$C_8$ alkyl" and "$C_1$–$C_6$ alkyl" groups specified herein include straight chain or branched chain hydrocarbon radicals having from one to eight and from one to six carbon atoms respectively. Illustrative of such alkyl groups include methyl, ethyl, propyl, isopropyl, butyl, isobutyl, sec-butyl, tert-butyl, pentyl, neopentyl, hexyl, isohexyl, octyl and the like.

Illustrative of the groups represented by the term "$C_1$–$C_6$ alkoxy" include straight chain or branched chain alkoxy radicals having from one to six carbon atoms. Representative of such groups include, for example, methoxy, ethoxy, propoxy, isopropoxy, butoxy, t-butoxy, pentoxy, hexoxy and the like.

The term "substituted phenyl" as used herein refers to phenyl moieties having one or two substituents selected from the class consisting of halo and $C_1$–$C_6$ alkoxy. Illustrative of such substituted phenyl groups include 4-chlorophenyl, 2,4-dichlorophenyl, 3-bromophenyl, 2-methoxyphenyl, 4-methoxyphenyl, 3-methoxyphenyl, 3,4-dimethoxyphenyl, 3,5-diethoxyphenyl, 2-chloro-4-methoxyphenyl and the like.

As used herein the term "halogen or halo" refers to fluoro, chloro, iodo and bromo.

The compounds of the present invention wherein $R^1$ is hydrogen, $C_1$–$C_6$ alkyl, benzyl or phenyl may be prepared in accordance with the following general procedure:

A dihydroimidazole of the formula (II)

H—N⌐⌐N
       \\
        CH$_2$
        |
        R$^2$ wherein $R^2$ is above defined, is reacted with a substituted nitroaromatic of the formula (III)

Z—X—Z
 \\    \\
  R$^3$   NO$_2$ wherein Z is halo; and X and $R^3$ are above defined; under basic conditions in an appropriate solvent such as isopropyl alcohol or acetonitrile, to yield a dihydroimidazo[1,2,-a]quinoxaline of the formula:

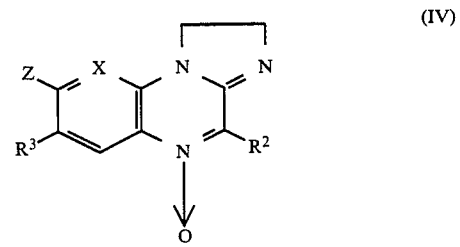

(IV)

The dihydroimidazo[1,2,-a]quinoxaline of the formula (IV) is reacted with an N-substituted piperazine of the formula

(V)

wherein $R^7$ is hydrogen, $C_1-C_6$ alkyl, benzyl or phenyl; in an appropriate solvent at a temperature of from 70° C. to 100° C. to yield the compounds of the formula:

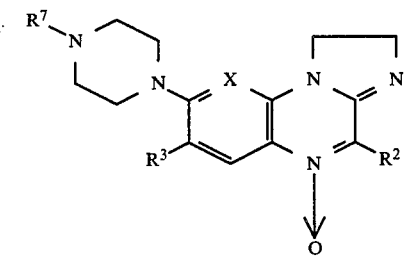

(VI)

The product may be utilized as is or recrystallized using an appropriate solvent applying conventional techniques.

To prepare the compounds of formula (I) wherein $R^1$ is a

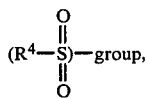

group, a compound of formula (VI) wherein $R^7$ is hydrogen is reacted with a sulfonylhalide of the formula

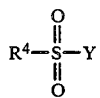

(VII)

wherein Y is halo and $R^4$ is above defined; in an appropriate solution.

To prepare the compounds of formula (I) wherein $R^1$ is a

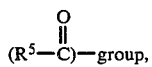

group, a compound of formula (VI), wherein $R^7$ is hydrogen, is reacted with an acid of the formula:

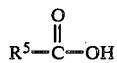

(VIII)

wherein $R^5$ is above defined; in the presence of a diphenylphosphorylazide.

A preferred embodiment includes compounds of the formula

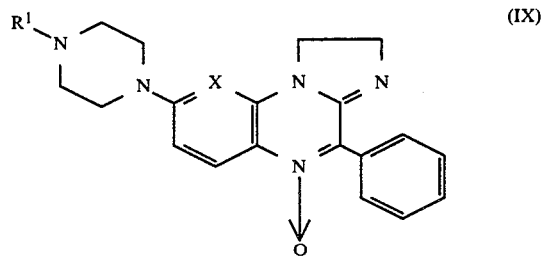

(IX)

wherein X and $R^1$ are above defined.

A more preferred embodiment encompasses compounds of formula (IX) wherein $R^1$ is $C_1-C_6$ alkyl or benzyl and X is above defined and most preferred are compounds of formula (IX) wherein $R^1$ is methyl and X is —N—.

The appropriate solvents employed in the above reactions are solvents wherein the reactants are soluble but do not react with the reactants. The preferred solvents vary from reaction to reaction and are readily ascertained by one of ordinary skill in the art.

The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art.

Accordingly, the invention provides a class of novel pharmaceutical compositions comprising one or more compounds of the present invention in association with one or more non-toxic, pharmaceutically acceptable carriers and/or diluents and/or adjuvants (collectively referred to herein as "carrier" materials) and if desired other active ingredients. The compounds and composition may for example be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit contained in a particular amount of the active ingredient. Examples of such dosage units are tablets or capsules. These may with advantage contain an amount of active ingredient from about 1 to 250 mg preferably from about 25 to 150 mg. A suitable daily dose for a mammal may vary widely depending on the condition of the patient and other factors. However, a dose of from about 0.1 to 300 mg/kg body weight, particularly from about 1 to 100 mg/kg body weight may be appropriate.

The active ingredient may also be administered by injection as a composition wherein, for example, saline, dextrose or water may be used as a suitable carrier. A suitable daily dose is from about 0.1 to 100 mg per kg body weight injected per day in multiple doses depending on the disease being treated. A preferred daily dose would be from about 1 to 30 mg/kg body weight.

The dosage regimen for treating an infectious disease condition with the compounds and/or compositions of this invention is selected in accordance with a variety of factors, including the type, age, weight, sex and medical condition of the patient; the severity of the infection;

the route of administration; and the particular compound employed and thus may vary widely.

For therapeutic purposes, the compounds of this invention are ordinarily combined with one or more adjuvants appropriate to the indicated route of administration. If per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and thus tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art. Appropriate dosages, in any given instance, of course depend upon the nature and severity of the condition treated, the route of administration, and the species of mammal involved, including its size and any individual idiosyncrasies.

Representative carriers, diluents and adjuvants include for example, water, lactose, gelatin, starches, magnesium stearate, talc, vegetable oils, gums, polyalkyline glycols, petroleum jelly, etc. The pharmaceutical compositions may be made up in a solid form such as granules, powders or suppositories or in a liquid form such as solutions, suspensions or emulsions. The pharmaceutical compositions may be subjected to conventional pharmaceutical operations such as sterilization and/or may contain conventional pharmaceutical adjuvants such as preservatives, stabilizers, wetting agents, emulsifiers, buffers, etc.

As previously mentioned, the compounds and compositions of the present invention are effective as antianaerobic agents for the treatment of infectious diseases related to anaerobic bacteria. Representative of infectious diseases that may be treated with the compounds and compositions of the present invention include, for example, post operative sepsis following lower gastrointestinal surgery or female urinogenital surgery, pelvic inflammatory disease, ulcers and gangrene, trichomonal vaginitis, non-specific vaginitis, amoebiasis, giardiasis, periodontal disease, acne and the like.

The following Examples are intended to further illustrate the present invention and not to limit the invention in spirit or scope. In the Examples, all parts are parts by weight unless otherwise expressly set forth.

EXAMPLE 1

1,2-Dihydro-8-fluoro-4-phenylimidazo[1,2-a]quinoxaline 5-oxide

A mixture of tolazoline (40 g, 0.25 mol), 2,4-difluoronitrobenzene (39.75 g, 0.25 mol) and potassium carbonate (17.26 g, 0.125 mol) in isopropanol (500 ml) was heated to 50° C. for a period of two days. The solvent was removed in vacuo from the mixture and the residue was dissolved in dichloromethane. The resulting solution was filtered and the solvent removed in vacuo to yield a yellow solid which was chromatographed on silica gel using 2% methanol/chloroform as the eluent to yield 1,2-dihydro-8-fluoro-4-phenylimidazo[1,2-a]quinoxaline 5-oxide (38.5 g) as an orange solid, having a m.p. 188°–193° C., (Found: C, 68.07; H 4.23; N 14.82%; $C_{16}H_{12}FN_3O$ requires C 68.33; H 4.27; N 14.95%) and represented by the structural formula

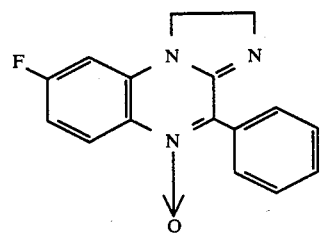

EXAMPLES 2-3

The following compounds were prepared in accordance with the procedure of Example 1 utilizing the appropriate nitroaromatic in lieu of the 2,4-difluoronitrobenzene.

EXAMPLE 2

1,2-Dihydro-7,8-difluoro-4-phenylimidazo[1,2-a]quinoxaline 5-oxide;—orange solid, m.p. 212°–213° C. (Found: C, 63.28; H, 3.65; N 13.72%; $C_{16}H_{11}F_2N_3O.0.2H_2O$ requires C, 63.45; H, 3.76; N 13.88%) represented by the structural formula:

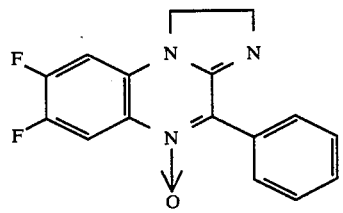

EXAMPLE 3

8-Chloro-1,2-dihydro-4-phenylimidazo[1,2-a]pyrido[3,2-e]-pyrazine 5-oxide;—yellow needles, m.p. 170°–171° C. (Found: C, 60.14; H,3.61; N,18.52%; $C_{15}H_{11}ClN_4O$ requires C,60.40; H, 3.69; N,18.79%) represented by the structural formula:

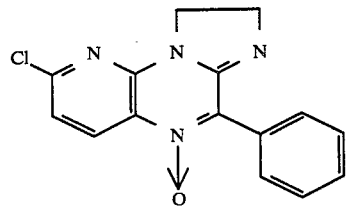

EXAMPLE 4

1,2-Dihydro-8-(4-methylpiperazinyl)-4-phenylimidazo[1,2-a]-quinoxaline 5-oxide;

1,2-Dihydro-8-fluoro-4-phenylimidazo[1,2-a]quinoxaline 5-oxide (3.5 g, 0.012 mol) and N-methylpiperazine (15 ml, 0.13 mol) were heated at 100° C. in isopropanol (5 ml) for 16 hrs. The solvent was removed in vacuo and the residue was dissolved in dichloromethane. The resulting solution was washed with saturated aqueous sodium hydrogen carbonate, dried over anhydrous magnesium sulphate and concentrated in vacuo to yield a dark oil which was chromatographed on silica gel in 2% methanol/chloroform to yield a red solid. The red solid was recrystallized from ethyl acetate to yield 1,2-dihydro-8-(4-methylpiperazinyl)-4-phenylimidazo[1,2-a]quinoxaline 5-oxide, (0.75 g), as deep red crystals m.p. 179°–183° C., (δ(CDCl₃) 2.38 (3H,s) 2.58 (4H,m) 3.37 (4H,m) 3.95-4.24 (4H,m) 6.08 (1H,d,J=3.5Hz), 6.62 (1H,dd,J=9 and 3.5Hz), 7.38-7.5 (3H,m), 7.84 (2H,m), and 8.11 (1H,d,J=9 Hz)), represented by the structural formula:

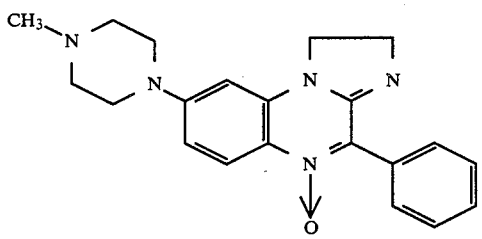

EXAMPLES 5–10

The following compounds were prepared in accordance with the reaction conditions employed in Example 4 using appropriate starting materials;

EXAMPLE 5

1,2-Dihydro-7-fluoro-4-phenyl-8-(4-phenylpiperazinyl)imidazo[1,2-a]quinoxaline 5-oxide;—deep red crystals, m.p. 201°–205° C. (Found: C,70.99; H,5.30; N,15.81%; $C_{26}H_{24}FN_5O$ requires C,70.75; H,5.44; N,15.87%) represented by the structural formula:

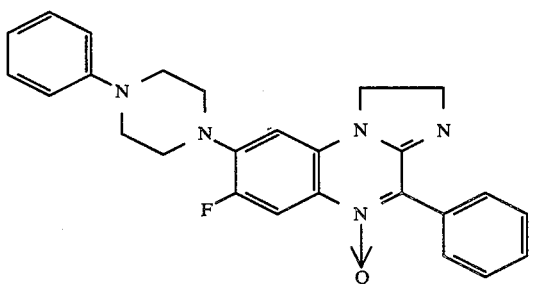

To prepare the compound of Example 5, the reaction in the procedure of Example 4 was conducted at a temperature of 70° C. rather than at 100° C.

EXAMPLE 6

1,2-Dihydro-4-phenyl-8-(4-phenylmethylpiperazinyl)imidazo[1,2-a]quinoxaline 5-oxide;—red needles, m.p. 205°–210° C. (Found: C,73.80; H,6.30; N,15.59%; $C_{27}H_{27}N_5O$ requires C, 74.14; H 6.18; N,16.02%) represented by the structural formula:

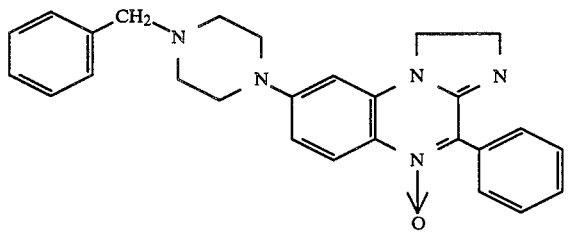

To prepare the compound of Example 6 the reaction in the procedure of Example 4 required three days to go to completion rather than 16 hours.

EXAMPLE 7

8-(4-Acetylpiperazinyl)-1,2-dihydro-4-phenylimidazo[1,2-a]quinoxaline 5-oxide;—red crystals, m.p. 145°–147° C. (Found: C,67.67; H,5.91; N, 17.90%; $C_{22}H_{23}N_5O_2$ requires C,67.87: H,5.91; N;17.99%) represented by the structural formula:

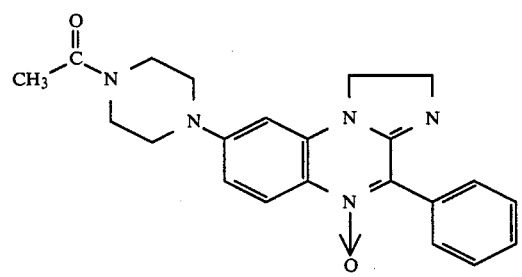

To prepare the compound of Example 7 the reaction in the procedure of Example 4 required four days to go to completion rather than 16 hours.

EXAMPLE 8

1,2-Dihydro-4-phenyl-8-(4-phenylpiperazinyl)imidazo[1,2-a]quinoxaline 5-oxide;—yellow solid, m.p. 243°–244° C. (Found: C,73.15; H,5.86; N,16.31%; $C_{26}H_{25}N_5O.0.2H_2O$ requires C, 73.13; H,5.86; N,16.40%) represented by the structural formula:

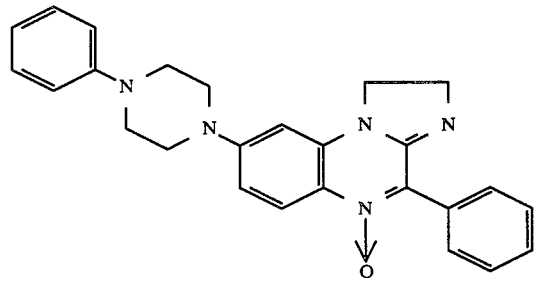

To prepare the compound of Example 8, the procedure of Example 4 was conducted utilizing neat N-phenylpiperazine in lieu of N-methylpiperazine in isopropanol and the reaction was conducted at a temperature of 120° C., for 3 hrs.

EXAMPLE 9

1,2-Dihydro-8-(4-methylpiperazinyl)-4-phenylimidazo[1,2-a]pyrido[3,2-e]pyrazine 5-oxide;—orange-red solid, m.p. 138°–142° C. (Found: C,66.04; H,6.07; N,22.95%; $C_{20}H_{22}N_6O$ requires C,66.30; H,6.08; N,23.20%), represented by the structural formula:

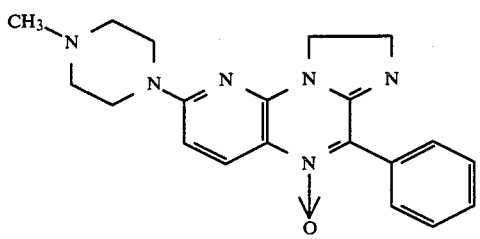

To prepare the compound of Example 9 the reaction in the procedure of Example 4 was conducted at a temperature of 60° C., for 30 min., rather than at 100° C. for 16 hrs.

EXAMPLE 10

8-(4-Acetylpiperazinvl)-1,2-dihydro-4-phenylimidazo[1,2-a]pyrido[3,2-e]pyrazine 5-oxide; an orange solid, m.p. 252°–254° C. (Found: C, 63.80; H, 5.62; N, 20.95%; $C_{21}H_{22}N_6O_2 \cdot 0.3H_2O$ requires C, 63.73; H, 5.71; N, 21.24%), represented by the structural formula:

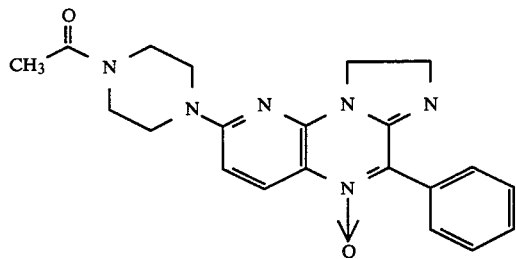

To prepare the compound of Example 10 the reaction in the procedure of Example 4 was conducted at a temperature of 85° C. for three days rather than at 100° C. for 16 hrs. In addition, one molar equivalent of triethylamine was added to the reaction mixture before heating commenced.

EXAMPLE 11

1,2-Dihydro-4-phenyl-8-piperazinylimidazo[1,2a]-quinoxaline 5-oxide

Under a nitrogen atmosphere, 1,2-dihydro-8-fluoro-4-phenylimidazo[1,2-a]quinoxaline 5-oxide (40 g 0.142 mol) and piperazine (122 g, 419 mol) were heated at 9° C., for 3.5 hrs. The solvent was removed in vacuo and the resulting residue was dissolved in dichloromethane. The resulting solution was washed with water, dried over anhydrous magnesium sulphate and concentrated in vacuo to yield an orange solid. The orange solid was recrystallized from chloroform-ethyl acetate to yield 1,2-dihydro-4-phenyl-8-piperazinylimidazo[1,2-a]quinoxaline 5-oxide, (45 g) as orange crystals, m.p. 209°–211° C. (Found: C, 68.56; H,6.06; N,19.99%; $C_{20}H_{21}N_5O \cdot 0.2H_2O$ requires C, 68.43; H,6.14; N,19.95%) represented by the structural formula:

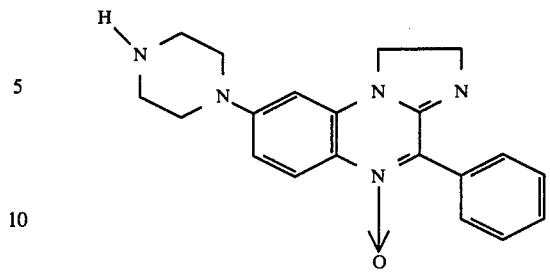

EXAMPLE 12

1,2-Dihydro-8-(4-octanoylpiperazinyl)-4-phenylimidazo[1,2-a]quinoxaline 5-oxide

To a stirred suspension of 1,2-dihydro-4-phenyl-8piperazinylimidazo [1,2-a]quinoxaline 5-oxide (1.5 g, 0.0043 mol) in dimethylformamide (20 ml) under an atmosphere of nitrogen and cooled in an ice-bath, was added octanoic acid (0.67 g, 0.0043 mol.) and diphenylphosphorylazide (1.29 g, 0.0047 mol). The reaction mixture was allowed to stand for 15 minutes. Triethylamine (0.95 g, 0.0047 mol) was added to the reaction mixture and the resulting mixture was allowed to stand for 1 hr, then warmed to room temperature over an additional 1 hr period. The solvent was removed in vacuo and the residue was dissolved in chloroform. The solution was washed with saturated aqueous sodium hydrogen carbonate and then water, dried over anhydrous magnesium sulphate and concentrated in vacuo to yield an orange solid. The orange solid was recrystallized from chloroform:ethyl acetate to yield 1,2-dihydro-8-(4-octanoylpiperazinyl)-4-phenylimidazo[1,2-a]quinoxaline 5-oxide, (1.6 g) as yellow crystals, m.p. 212°–213° C. (Found: C,70.72; H,7.44; N,14.77%; $C_{28}H_{35}N_5O_2$ requires C,71.01; H,7.45; N,14.78%), represented by the structural formula:

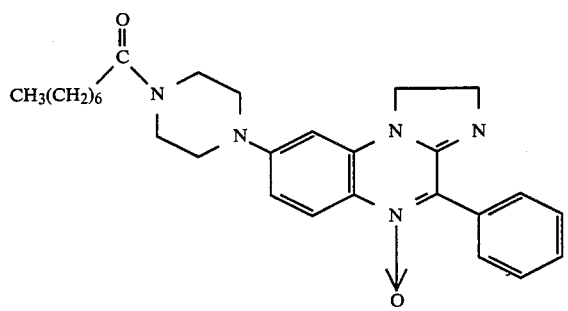

EXAMPLES 13–16

The following compounds were prepared in accordance with the reaction conditions employed in Example 12 using appropriate starting materials.

EXAMPLE 13

1,2-Dihydro-4-phenyl-8-[4-(2-phenylacetyl)-piperazinyl]imidazo[1,2-a]quinoxaline 5-oxide;—orange crystals, m.p. 144°–146° C. (Found: C, 69.36, H, 5.64; N, 14.11%; $C_{28}H_{27}N_5O_2$ Requires: C, 69.55; H, 6.04; N, 14.48%) having the formula:

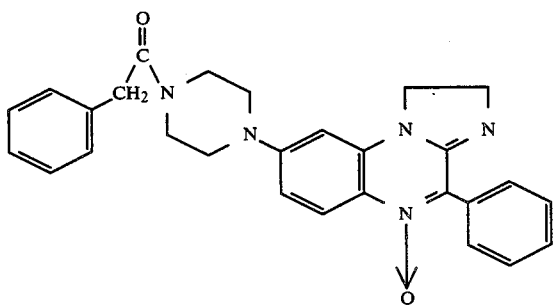

EXAMPLE 14

1,2-Dihydro-8-[4-[N-[(1,1-dimethylethoxy)carbonyl]-glycinyl]piperazinyl]-4-phenylimidazo[1,2-a]quinoxaline 5-oxide;—orange crystals, m.p. 210°–212° C. C,64.09; H,6.37; N,16.37%; $C_{27}H_{32}N_6O_4$ requires C 64.40; H,6.20; N,16.69%) having the formula:

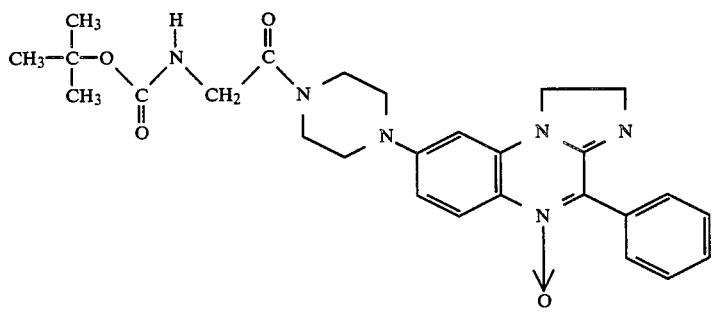

EXAMPLE 15

8-(4-Benzoylpiperazinyl)-1,2-dihydro-4-phenylimidazo[1,2-a]quinoxaline 5-oxide;—orange crystals, m.p. 225°–230° C. (Found: C,71.09; H,5.54; N,15.36%; $C_{27}H_{25}N_5O_2.0.3H_2O$ requires C,70.97; H,5.65; N,15.33%) represented by the structural formula:

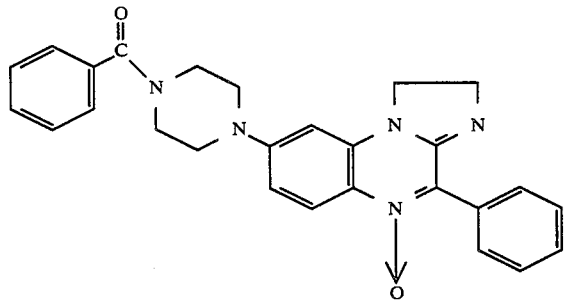

EXAMPLE 16

1,2-Dihydro-4-phenyl-8-[4-(2-pyridinecarbonyl)-piperazinyl]imidazo[1,2-a]quinoxaline 5-oxide;—orange crystals, m.p. 230°–235° C. (Found: C,68.27; H,5.28; N,18.41%; $C_{26}H_{24}N_6O_2.0.3H_2O$ requires C,68.20; H,5.41; N,18.35%) represented by the structural formula:

EXAMPLE 17

1,2-Dihydro-4-phenyl-8-(4-phenylmethylpiperazinyl)imidazo[1,2-a]pyrido[3,2-e]pyrazine 5-oxide 8-Chloro-1,2-dihydro-4-phenylimidazo[1,2-a]pyrido[3,2-e]pyrazine 5-oxide (3 g, 0.01 mol) and benzylpiperazine (3.6 g, 0.02 mol) were heated at 80° C., in isopropanol (100 ml) under an atmosphere of nitrogen for 16 hrs. As the reaction mixture cooled to room temperature, a yellow solid precipitated. The yellow solid was collected by filtration, washed with cold isopropanol and recrystallized from isopropanol to yield 1,2-dihydro-4-phenyl-8-(4-phenylmethylpiperazinyl)imidazo[1,2-a]pyrido[3,2-e]pyrazine 5-oxide (3.7 g), as orange needles, m.p. 184°–187° C. (Found: C,71.03; H,6.02; N,19.30%; $C_{26}H_{24}N_6O.0.1H_2O$ requires C,70.92; H,6.00; N,19.09%), represented by the structural formula:

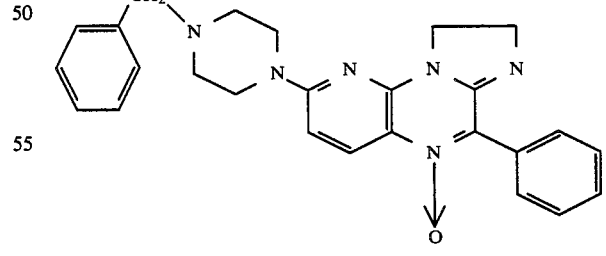

EXAMPLE 18

1,2-Dihydro-8-(4-(methylsulphonyl)piperazinyl)-4-phenylimidazo[1,2-a]quinoxaline 5-oxide A solution of methanesulfonyl chloride (0.33 g, 0.003 mol) in dichloromethane (20 ml) was cooled in an ice-bath. To this solution was added dropwise with stirring, a solution of triethylamine (0.29 g, 0.003 mol) and 1,2- dihydro-4-phenyl-8-piperazinylimidazo[1,2-a]quinoxaline 5-oxide (1 g, 0.003 mol) in dichloromethane (10 ml). The reaction mixture was stirred for an additional 15 minutes and then was allowed to warm to room temperature. The reaction mixture was washed with water, dried over anhydrous magnesium sulphate and then evaporated to dryness under reduced pressure to yield a yellow solid. Recrystallization from ethyl acetate yielded 1,2-dihydro-8-(4-(methylsulphonyl)-piperazinyl)-4-phenylimidazo[1,2-a]quinoxaline 5-oxide (0.8 g), as yellow crystals, m.p. 252°–253° C. (Found: C,59.19; H,5.35; N,16.33%; $C_{21}H_{23}N_5O_3S$ requires C,59.29; H,5.41; N,16.47%) having the formula:

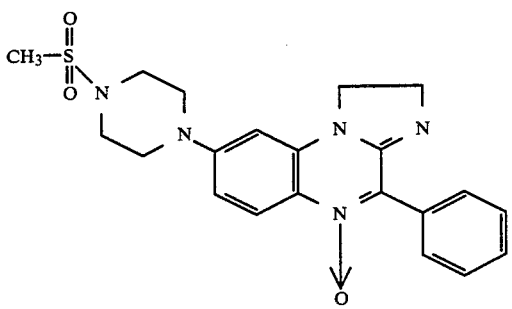

EXAMPLE 19

2-[4-(1,2-Dihydro-5-oxido-4-phenylimidazo[1,2-a]quinoxalin-8-yl)piperazinyl]acetamide Triethylamine (0.75 g, 0.0072 mol.) was added to a solution of iodoacetamide (0.59 g, 0.0032 mol.) and 1,2-dihydro-4-phenyl-8-piperazinylimidazo[1,2-a]quinoxaline 5-oxide (1.0 g, 0.0029 mol.) in ethanol (50 ml) and the reaction mixture stirred overnight at room temperature. The resulting precipitate was removed by filtration, washed with ethanol and then ether. Recrystallization from ethanol yielded 2-[4-(1,2-dihydro-5-oxido-4-phenylimidazo[1,2-a]-quinoxalin-8-yl)piperazinyl]acetamide, (0.63 g) as bright yellow crystals, m.p. 225°–227° C. (Found: C, 63.50; H, 5.89; N, 19.72%; $C_{22}H_{24}N_6O_6 \cdot 0.75H_2O$ requires C, 63.23; H, 6.11; N, 20.12%) represented by the structural formula:

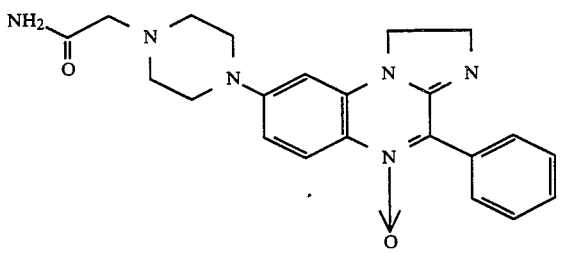

EXAMPLE 20

The screening panel utilized in this Example consisted of 5 strains of Bacteroides fragilis. All assays were carried out in 96 well microtitre plates. If an isolate was obtained from either a culture collection or clinical source, the isolate was immediately inoculated into Wilkins-Chalgren broth (Oxoid) and incubated at 37° C. in an anaerobic chamber in an atmosphere of 85% nitrogen, 10% carbon dioxide, and 5% hydrogen for 48 hours. At the end of this time, the viable count was about $10^{12}$ organisms/ml broth. A 1 ml aliquot of each culture was placed in an ampoule and quick frozen in acetone-dry ice mixture and stored in liquid nitrogen. When an inoculum was utilised in an assay, one of the ampoules was thawed and diluted with fresh broth to yield a suspension having a count of $5 \times 10^5$ organisms/ml. A 100 μl aliquot of the suspension was inoculated into each well of the microtitre plate.

A 2 mg sample of the test compound was dissolved in 0.2 ml of a suitable solvent such as dimethylsulphoxide, polyethylene glycol 200 or methanol. The solution was then diluted with 4.8 ml of water to yield a solution having a concentration of 400 mg/L. Doubling dilutions of this stock were prepared to give a range of concentrations from 1.6–200 mg/L. 100 μl of each concentration were then placed in the wells of the microtitre plate containing the inoculum, to produce a mixture having a final concentration in the range of 0.8–100 mg/L. Metronidazole was employed as a positive control and a solvent/water mixture was employed as a negative control. After addition of the test solution the final inoculum level was $10^5$ cells/ml. The plates were incubated for 48 hours at 37° C. in the anaerobic chamber. The Minimum Inhibitory Concentration (MIC) was read visually. The MIC is defined as the lowest concentration at which there is no detectable growth. The Minimum Bactericidal Concentration (MBC) was determined by taking 50 μl aliquot from each well and placing it in fresh medium. The MBC is defined as the lowest concentration at which there is less than 5 colonies (i.e., 99.9% reduction in viable count) after 48 hours of incubation. The MIC and MBC values for each compound tested and the respective MIC and MBC value for metronidazole are indicated in Table 1. The MIC and MBC value for the negative control that was assayed along with each test compound was greater than 100 mg/L. The MIC and MBC values in Table 1 are expressed in mg/L. A blank in the table represented by a "-" indicates that the assay was not conducted using the strain indicated.

The strains of Bacteroides fragilis utilized in the above procedure are identified by letter in accordance with the following legend:

| STRAIN | ORGANISM |
|---|---|
| A | B. fragilis NCTC 10581 |
| B | B. fragilis NCTC 9343 |
| C | B. fragilis NCTC 9344 |
| D | B. fragilis MZ-R ATCC 11295 |
| E | B. fragilis WS-1* |

*Obtained from St. Thomas's Hospital Medical School, London, United Kingdom.

TABLE 1

| COMPOUND OF EXAMPLE NO. | STRAIN | | | | | | | | | |
|---|---|---|---|---|---|---|---|---|---|---|
| | A | | B | | C | | D | | E | |
| | MIC | MBC | MIC | MBC | MIC | MBC | MIC | MBC | MIC | MBC |
| 1 | 3.1 | 3.1 | 3.1 | 3.1 | 1.5 | 1.5 | 0.8 | 1.5 | 3.1 | 3.1 |
| Metronidazole | 0.6 | 0.8 | 0.8 | 1.5 | 0.6 | 0.6 | 3.1 | 6.2 | 1.5 | 3.1 |

TABLE 1-continued

| COMPOUND OF EXAMPLE NO. | STRAIN | | | | | | | | | |
|---|---|---|---|---|---|---|---|---|---|---|
| | A | | B | | C | | D | | E | |
| | MIC | MBC | MIC | MBC | MIC | MBC | MIC | MBC | MIC | MBC |
| 2 | 0.6 | 0.6 | 0.15 | 0.15 | 0.6 | 0.6 | 0.08 | 0.15 | 0.6 | 0.6 |
| Metronidazole | 0.6 | 0.8 | 0.6 | 0.8 | 0.6 | 0.8 | 6.2 | 12.5 | 1.5 | 1.5 |
| 3 | 12.5 | 12.5 | 12.5 | 12.5 | 6.2 | 6.2 | 3.1 | 3.1 | 6.2 | 6.2 |
| Metronidazole | <0.8 | <0.8 | <0.8 | <0.8 | <0.8 | <0.8 | 6.2 | 12.5 | <0.8 | <0.8 |
| 4 | 3.1 | 3.1 | 3.1 | 3.1 | 3.1 | 3.1 | 1.5 | 1.5 | 6.2 | 6.2 |
| Metronidazole | 0.8 | 0.8 | 1.5 | 3.1 | 0.8 | 0.8 | 12.5 | 12.5 | 0.8 | 0.8 |
| 5 | 3.1 | — | 1.5 | — | 6.2 | — | 0.8 | — | 1.5 | — |
| Metronidazole | 0.8 | — | 0.8 | — | 0.8 | — | 6.2 | — | 0.8 | — |
| 6 | 25 | 25 | 50 | 50 | 12.5 | 25 | 25 | 25 | 25 | 25 |
| Metronidazole | 1.5 | 1.5 | 1.5 | 1.5 | <0.8 | <0.8 | 12.5 | 12.5 | 1.5 | 3.1 |
| 7 | 6.2 | 6.2 | 3.1 | 3.1 | 6.2 | 6.2 | 1.5 | 1.5 | 6.2 | 6.2 |
| Metronidazole | 0.6 | 0.8 | 0.6 | 0.8 | 0.6 | 0.8 | 6.2 | 12.5 | 1.5 | 1.5 |
| 8 | 1.5 | — | 1.5 | — | <0.8 | — | <0.8 | — | 3.1 | — |
| Metronidazole | <0.8 | — | <0.8 | — | <0.8 | — | 6.2 | — | <0.8 | — |
| 9 | 0.8 | 0.8 | 0.8 | 0.8 | 0.8 | 0.8 | 0.8 | 0.8 | — | — |
| Metronidazole | 0.8 | 0.8 | 0.8 | 1.5 | 0.8 | 0.8 | 6.2 | 2.5 | — | — |

EXAMPLE 21

Utilizing the procedures described in Example 20, the anti-anaerobic activity of certain compounds of the present invention was demonstrated utilizing an additional 10 strains of various anaerobic bacteria.

The MIC values obtained are indicated in Table 2. A blank in the table represented by a "-" indicates that the assay was not conducted using the strain indicated.

was kept to a minimum. Cultures were incubated anaerobically in an anaerobic chamber. When the broths reached a heavy turbidity (24–48 hours) they were aliquoted into small bottles, inactivated horse serum added to 10%, together with a few drops of neutralized ascorbate (100 mg/ml) before snap freezing and storing at −20° C. The viable count was $10^{10}$ organisms/ml.

Rat faeces or mouse bowel contents were mixed with a small volume of water and autoclaved then homoge-

TABLE 2

| | MIC vs. PANEL OF ANAEROBES | | | | | | | | |
|---|---|---|---|---|---|---|---|---|---|
| | Compound of Example No. | | | | | | | | |
| Organism | (1) | (2) | (3) | (4) | (5) | (6) | (7) | (8) | MZ* |
| Clostridium perfringens NCTC 523 | 3.1 | 6.2 | 6.2 | 6.2 | 3.1 | 12.5 | 1.5 | 1.5 | <0.8 |
| Clostridium perfringens NCTC 8237 | 3.1 | 6.2 | 25 | 12.5 | 6.2 | 12.5 | 3.1 | 3.1 | 1.5 |
| Clostridium difficile NCIB 10666 | <0.8 | <0.8 | <0.8 | 1.5 | <0.8 | <0.8 | <0.8 | <0.8 | <0.8 |
| Clostridium difficile Cytotoxic 1 | <0.8 | 6.2 | <0.8 | 6.2 | <0.8 | 3.1 | <0.8 | <0.8 | <0.8 |
| Campylobacter fetus ss.jejuni ATCC 29428 | 2.5 | 12.5 | 50 | 25 | >100 | 100 | 12.5 | >100 | >100 |
| Fusobacterium necrophorum ATCC 11295 | <0.8 | 3.1 | 6.2 | 6.2 | 6.2 | 12.5 | 3.1 | 3.1 | 6.2 |
| Bacteroides melanogenicus NCTC 9336 | 25 | 6.2 | 100 | 12.5 | >100 | 50 | 6.2 | >100 | >100 |
| Peptostreptococcus anaerobicus | 25 | 12.5 | 50 | 12.5 | >100 | 100 | 12.5 | >100 | >100 |
| Propionebecterium acnes NCTC 737 | 50 | 25 | >100 | 25 | >100 | 50 | 25 | >100 | >100 |
| Propionebacterium acnes NCTC 7337 | 50 | 25 | 100 | 25 | >100 | 50 | 12.5 | >100 | >100 |

*MZ = Metronidazole

EXAMPLE 22

Determination of in vivo Anti-anaerobe activity—mouse hepatic necrosis 500 ml volumes of basic anaerobe broth (nutrient broth No. 2 (LAB M) 28 g/L, haemin 5 mg/L, vitamin K 0.5 mg/L, and cysteine hydrochloride 0.5 g/L) were inoculated from a cooked meat broth stock culture of B. Fragilis ATCC 23745 which had been inoculated from the original cooked meat broth stock i.e. subculturing nised. After standing overnight they were autoclaved again and then freeze-dried in small batches.

Stock inoculum was thawed and diluted to yield a viable count of $5 \times 10^8$ organisms/ml with fresh broth, and sterile faecal material was added to a final concentration of 2% w/v. Animals (groups of ten male BALBLc mice weighing 18–22 g) were inoculated intraperitoneally with 0.2 ml of the inoculum so that each receives $10^8$ *B. fragilis.*

Test compounds were dissolved in polyethylene glycol 200 or dimethylsulphoxide and then diluted with water or saline to give the appropriate final concentration. The stock solution was used to prepare a two-fold dilution series having a final dose range of 2.5-40 mg/kg. The initial dose was given p.o. immediately after infection and twice daily thereafter for 2 days. Animals were sacrificed on the third day using carbon dioxide or cervical dislocation. Control animals received dosing vehicle only. Metronidazole was used as a positive control.

At the end of the experimental period the animals' livers were removed aseptically with care not to puncture the bowel, and transferred to Universal bottles of peptone water and kept on ice.

The livers were homogenized at low speed with care to prevent frothing and the bottles were gassed out again. Homogenate was diluted by transferring 0.1 ml of the homogenate to a 10 ml aliquot of peptone water diluent, and the diluted homogenate was spread on basic anaerobic agar at 0.1 ml per petri-dish. The media used for this purpose must have either been prepared freshly, or stored in plastic bags in which the air has been replaced by anaerobic gas mixture, or stored in anaerobic jars. After the homogenate was spread on the petri-dishes, the petri-dishes were left exposed to air for the minimum possible time (and never more than 15 minutes) so that small numbers of Bacteroides were recovered and grown from the inoculum.

Cultures were incubated anaerobically for 48 hrs. in a Forma Anaerobic Chamber at 37° C. At the end of this period, the resultant colonies were counted using an AMS 40-10 Image Analyser. The mean number of viable organisms were calculated for each treatment group and the data analysed using Analysis of varience and two sample t-test for comparison of individual groups. Results were expressed as the reduction in log colony forming units/ml of liver homogenate for each treatment group compared to the untreated controls. From the dose response curves, the dose giving 1 log (90%) reduction is calculated for each compound and the efficacy of the test compound relative to metronidazole is determined.

Under these test conditions, metronidazole gives a reduction in *B. fragilis* of 3–3.5 $\log_{10}$ at 40 mg/kg (p.o.).

The activities of the compounds described above are given in Table 3.

TABLE 3

| Compound of Example No. | Dose giving 1 log reduction | | Metronidazole |
|---|---|---|---|
| | mg/kg | (mM/kg) | |
| (1) | 7.57 | (26.9) | 1.64 (9.6) |
| (2) | <40 | | 2.8 (12.7) |
| (3) | <40 | | 1.79 (10.46) |
| (4) | 7.73 | (22.0) | 2.49 (15.0) |
| (5) | 11.73 | (26.6) | 1.89 (11.06) |
| (6) | 6.27 | (14.34) | 2.29 (13.41) |
| (7) | 11.3 | (29.1) | 2.18 (12.7) |
| (9) | 4.48 | (12.4) | 1.95 (11.4) |
| (17) | 3.59 | (8.19) | 2.94 (17.2) |

Although this invention has been described with respect to specific modification, the details thereof are not to be construed as limitations, for it will be apparent that various equivalents, changes and modifications may be restored and modification may be resorted to without departing from the spirit and scope thereof and it is understood that such equivalent embodiments are intended to be included therein.

What is claimed is:

1. A compound of the formula

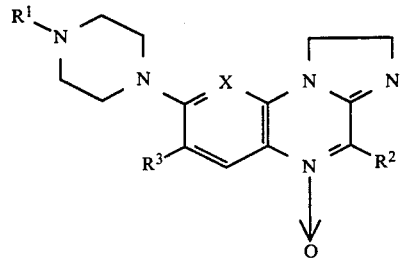

wherein
$R^1$ is $C_1$-$C_6$ alkyl, benzyl, phenyl, a

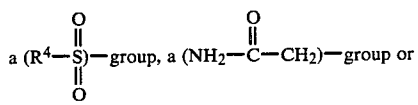

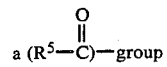

wherein $R^4$ is $C_1$-$C_6$ alkyl, and $R^5$ is $C_1$-$C_8$ alkyl, aminomethyl, pyridinyl, phenyl, halophenyl or a

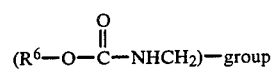

wherein $R^6$ is $C_1$-$C_6$ alkyl;
$R^2$ is phenyl or substituted phenyl having 1 or 2 substituents selected from the group consisting of halo or $C_1$-$C_6$ alkoxy;
$R^3$ is hydrogen or halogen; and
X is =CH— or =N—.

2. A compound according to claim 1 wherein $R^2$ is phenyl and $R^3$ is hydrogen.

3. A compound according to claim 2 wherein $R^1$ is $C_1$-$C_6$ alkyl or benzyl.

4. A compound according to claim 3 wherein X is =N—.

5. A compound according to claim 4 which is 1,2 dihydro-8-(4-methylpiperazinyl)-4-phenylimidazo[1,2-a]-pyrido[3,2-e]pyrazine 5-oxide.

6. A compound according to claim 4 which is 1,2-dihydro-4-phenyl-8-(4-phenylmethylpiperazinyl-)imidazo[1,2-a]pyrido[3,2-e]pyrazine 5-oxide.

7. A pharmaceutical composition comprising a therapeutically effective amount of a compound of the formula

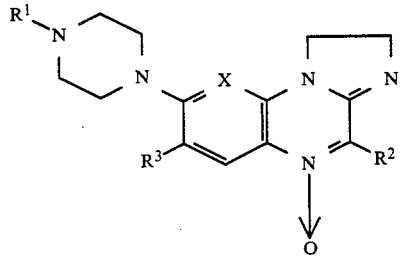

wherein
R¹ is C₁-C₆ alkyl, benzyl, phenyl,

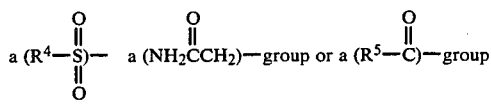

wherein R⁴ is C₁-C₆ alkyl, and R⁵ is C₁-C₈ alkyl, aminomethyl, pyridinyl, phenyl, halophenyl or a

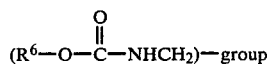

wherein R⁶ is C₁-C₆ alkyl;

R² is phenyl or substituted phenyl having 1 or 2 substituents selected from the group consisting of halo or C₁-C₆ alkoxy;

R³ is hydrogen or halogen; and

X is =CH— or =N—.

together with one or more non-toxic pharmaceutically acceptable carriers.

8. A pharmaceutical composition according to claim 7 wherein R² is phenyl and R³ is hydrogen.

9. A pharmaceutical composition according to claim 8 wherein R¹ is C₁-C₆ alkyl or benzyl.

10. A pharmaceutical composition according to claim 9 wherein X is =N—.

11. A pharmaceutical composition according to claim 10 wherein the compound is 1,2-dihydro-8-(4-methylpiperazinyl)-4-phenylimidazo[1,2-a]-pyrido[3,2-e]pyrazine 5-oxide.

12. A pharmaceutical composition according to claim 10 wherein the compound is 1,2-dihydro-4-phenyl-8-(4-phenylmethylpiperazinyl)imidazo[1,2-a]pyrido[3,2-e]pyrazine 5-oxide.

13. A method for treating an infectious disease in mammals caused by anaerobic bacteria comprising administering to a mammal in need of such treatment a therapeutically effective amount of a compound of the formula

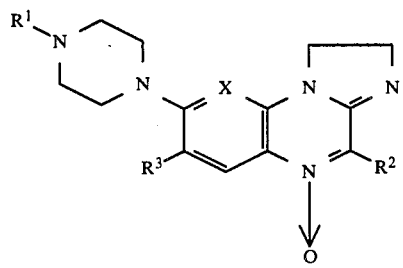

wherein
R¹ is C₁-C₆ alkyl, benzyl, phenyl,

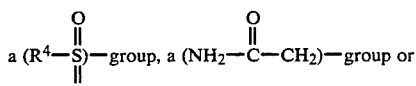

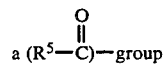

wherein R⁴ is C₁-C₆ alkyl, and R⁵ is C₁-C₈ alkyl, aminomethyl, pyridinyl, phenyl, halophenyl or a

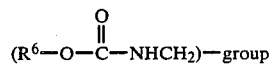

wherein R⁶ is C₁-C₆ alkyl;

R² is phenyl or substituted phenyl having 1 or 2 substituents selected from the group consisting of halo or C₁-C₆ alkoxy;

R³ is hydrogen or halogen; and

X is =CH— or =N—.

14. A method according to claim 13 wherein R² is phenyl and R³ is hydrogen.

15. A method according to claim 14 wherein R¹ is C₁-C₆ alkyl or benzyl.

16. A method according to claim 15 wherein X is =N—.

17. A method according to claim 16 wherein the compound is 1,2-dihydro-8-(4-methylpiperazinyl)-4-phenylimidazo[1,2-a]-pyrido[3,2-e]pyrazine 5-oxide.

18. A method according to claim 16 wherein the compound is 1,2-dihydro-4-phenyl-8-(4-phenylmethylpiperazinyl)imidazo[1,2-a]pyrido[3,2-e]pyrazine 5-oxide.

* * * * *

UNITED STATES PATENT AND TRADEMARK OFFICE
CERTIFICATE OF CORRECTION

PATENT NO. : 4,696,928

DATED : September 29, 1987

INVENTOR(S) : Ellames, et al.

It is certified that error appears in the above-identified patent and that said Letters Patent is hereby corrected as shown below:

Column 1, line 58, reading "of a" should read -- or a --.

Column 9, lines 55-56, reading "(122g, 419 mol) were heated at 9°C.," should read -- (122g, 1.419 mol) were heated at 90°C.,--.

Signed and Sealed this

Thirteenth Day of June, 1989

Attest:

DONALD J. QUIGG

*Attesting Officer*

*Commissioner of Patents and Trademarks*